United States Patent [19]

Clarke et al.

[11] Patent Number: 5,246,004
[45] Date of Patent: Sep. 21, 1993

[54] INFRARED CHOLESTEROL SENSOR

[75] Inventors: Richard H. Clarke, Big Sky, Mont.; Qian Wang, Boston, Mass.

[73] Assignee: Angiomedics II, Inc., Newton, Mass.

[21] Appl. No.: 929,941

[22] Filed: Aug. 14, 1992

Related U.S. Application Data

[63] Continuation-in-part of Ser. No. 649,477, Feb. 1, 1991, abandoned, which is a continuation-in-part of Ser. No. 474,344, Feb. 2, 1990, Pat. No. 5,054,487.

[51] Int. Cl.$^5$ ............................................. A61B 05/06
[52] U.S. Cl. .................................... 128/633; 128/666
[58] Field of Search ................... 128/633, 666; 356/41

[56] References Cited

U.S. PATENT DOCUMENTS

| | | | |
|---|---|---|---|
| 3,463,142 | 8/1969 | Harte | 128/2 |
| 3,638,640 | 2/1972 | Shaw | 128/2 |
| 3,958,560 | 5/1976 | March | 128/2 |
| 4,014,321 | 3/1977 | March | 128/2 |
| 4,169,676 | 10/1979 | Kaiser | 356/39 |
| 4,202,339 | 5/1980 | Wirtzfield et al. | 128/419 |
| 4,223,680 | 9/1980 | Jobsis | 128/633 |
| 4,350,163 | 9/1982 | Ford, Jr. et al. | 128/633 |
| 4,408,880 | 10/1983 | Tsuji et al. | 356/338 |
| 4,655,225 | 4/1987 | Dahne et al. | 128/633 |
| 4,704,029 | 11/1987 | Van Heuvelen | 356/39 |
| 4,714,080 | 12/1987 | Edgar, Jr. et al. | 128/633 |
| 4,785,814 | 11/1988 | Kane | 128/634 |
| 4,796,636 | 1/1989 | Branstetter et al. | 128/633 |
| 4,840,179 | 6/1989 | Ullrich | 128/633 |
| 4,854,699 | 8/1989 | Edgar, Jr. | 356/41 |
| 4,882,492 | 11/1989 | Schlager | 250/346 |
| 4,901,728 | 2/1990 | Hutchison | 128/633 |
| 4,975,581 | 12/1990 | Robinson et al. | 250/339 |
| 5,007,423 | 4/1991 | Branstetter et al. | 128/633 |
| 5,054,487 | 10/1991 | Clarke | 128/633 |
| 5,070,874 | 12/1991 | Barnes et al. | 128/633 |
| 5,086,229 | 2/1992 | Rosenthal et al. | 250/341 |

FOREIGN PATENT DOCUMENTS

| | | |
|---|---|---|
| 0160768 | 11/1985 | European Pat. Off. |
| 0282210 | 9/1988 | European Pat. Off. |
| 0282234 | 9/1988 | European Pat. Off. |
| 0404562 | 12/1990 | European Pat. Off. |
| WO90/07905 | 7/1990 | PCT Int'l Appl. |
| WO91/11136 | 8/1991 | PCT Int'l Appl. |
| 2075668 | 11/1981 | United Kingdom |
| 2033575 | 5/1989 | United Kingdom |

OTHER PUBLICATIONS

Giangiacomo et al., "Predicting Concentrations of Individual Sugars in Dry Mixtures by Near-Infrared Reflective Spectrascopy," Journal of Food Science, v. 46, pp. 531–534.

Mendelson et al., "Spectrophotometric Investigation of Pulsatile Blood Flow for Transcutaneous Reflectance Oximetry," Adv. Exp. Med. Biol., v. 159, pp. 93–102.

Osborne, "Applications of NIR in the Baking Industry," Anal. Proc., v. 20, pp. 79–83.

Peuchant et al., "Determination of Serum Cholesterol by Near-Infrared Reflectance Spectrometry," Anal. Chem. v. 59, pp. 1816–1819.

Polanyi et al., "In Vivo Oximeter with Fast Dynamic Response," The Review of Scientific Instruments v. 33, No. 10, pp. 1050–1054.

Steinke et al., "Reflectance Measurements of Hematocrit and Oxyhemoglobin Saturation," the American Physiological Society, pp. H147–H153.

Wilson et al., "Noninvasive Detection of Skeletal Muscle Underperfusion with Near-Infrared Spectroscopy in Patients with Heart Failure," Circulation v. 80, No. 6, pp. 1668–1674.

*Primary Examiner*—William E. Kamm
*Assistant Examiner*—Robert L. Nasser
*Attorney, Agent, or Firm*—Thomas J. Engellenner

[57] ABSTRACT

Systems and methods for non-invasive blood analysis are disclosed in which blood is illuminated at a plurality of discrete wavelengths selected from the near infrared spectrum. Measurements of the intensity of reflected or transmitted light at such wavelengths are taken, and an analysis of reflectance or transmittance ratios for various wavelengths is performed. Changes in the ratios can be correlated with specific material properties, such as the concentration of cholesterol in a subject's circulatory system.

27 Claims, 4 Drawing Sheets

INFRARED CHOLESTEROL SENSOR

REFERENCE TO RELATED APPLICATIONS

This application is a continuation-in-part of U.S. Ser. No. 649,477, filed Feb. 1, 1991, now abandoned which is a continuation-in-part of U.S. Ser. No. 474,344 filed Feb. 2, 1990, now U.S. Pat. No. 5,054,487 issued Oct. 8, 1991, both of which are incorporated herein by reference.

BACKGROUND OF THE INVENTION

The technical field of this invention is material analysis and, in particular, the invention relates to the detection and quantification of analytes in materials by measuring infrared absorptivity at multiple wavelengths.

Material analysis, especially the analysis of liquid materials for the presence of solutes, can be a tedious and complex task. In many instances, it would be more desirable to be able to analyze materials quickly, easily and non-invasively. One example of such an application is blood analysis.

Treatment of many medical disorders, particularly vascular conditions, can require accurate blood analysis. Additionally, in some situations, repeated or even continuous blood monitoring is desirable, for example, when monitoring cholesterol level variations.

Conventionally, blood is analyzed by withdrawing a sample from the body of a subject and examining it, using one or more techniques, such as immunoassays, activity assays, chromatographic assays and spectrophotometric assays. These conventional methods suffer from several common disadvantages. One such disadvantage is that these tests are invasive and raise the risk of patient infection and discomfort.

In addition, such tests can be time consuming. This time delay between when the blood is drawn and when the analysis is completed provides a window during which the subject's blood content may have changed, possibly leading to erroneous test results. A further disadvantage to conventional blood testing techniques is that the people drawing and testing the blood sample are put at risk for exposure to infectious disease agents.

Accordingly, it is the object of the present invention to provide an analytic apparatus for non-invasively, quickly and continuously detecting and quantifying cholesterol in a blood sample.

It is another object of this invention to provide a method and apparatus for non-invasive detection of blood-cholesterol levels but which avoids the problems of non-continuous test results, subject discomfort and potential technician exposure to infectious agents.

SUMMARY OF THE INVENTION

Systems and methods for non-invasive blood-cholesterol analysis are disclosed in which a blood sample in a vein, or in another vascularized area such as a nail bed, is non-invasively illuminated through a patient's tissue, such as the skin, at a plurality of discrete wavelengths, including a reference and a data wavelength. These wavelengths are preferably selected from the near infrared spectrum. Non-invasive measurements of the intensity of reflected or transmitted light at such wavelengths are taken, and a non-invasive analysis of reflectance or transmittance ratios is performed for various sets of these wavelengths. Changes in the detected ratios can be correlated with specific material properties, such as the concentration of cholesterol in a subject's circulatory system.

It has been discovered that cholesterol levels can be determined by measuring near infrared absorption at particular wavelengths. As used herein, the term "near infrared" or "near IR" is intended to encompass light in a spectrum ranging from about 1000 to about 2500 nm, more preferably from about 1300 to about 2400, and, in some instances, most preferably from about 1500 to about 2300 nm. Two especially useful wavelengths for cholesterol data readings are about 1720 nanometers (nm) and about 2300 nm.

One problem in obtaining reliable blood-analyte data is that the light impinged on the sample is scattered by various local properties of the subject. Accordingly, in another aspect of the invention, it has been discovered that more accurate analysis can be achieved by using a narrow window (e.g., closed spaced data and reference wavelengths) in order to eliminate or reduce the effect of light scattering caused by non-cholesterol analytes as well as the scattering effects of background and patient-dependent (e.g., skin pigmentation, thickness and vascular) factors that might otherwise interfere with accurate measurements.

By locating the data and reference wavelengths relatively close together, the effects of artifacts, such as scattering, can be minimized. Accordingly, in one preferred embodiment, the detection window (i.e., the distance between the data and reference wavelengths) is about 300 nanometers or less, more preferably about 100 nm or less, and in some instances most preferably less than about 30 nm. By choosing a data wavelength that is highly specific for cholesterol (i.e., with no competing nearby absorption peaks), the use of a narrow window also ensures that non-analyte absorption effects as well as scattering effects are minimized.

Furthermore, it has been discovered that light scattering increases as the interrogation wavelength approaches the visible light range. Therefore, in practice of the invention, two closely-spaced wavelengths are chosen, to assure a narrow window, and the window is preferably located at a relatively long wavelength, e.g., over 1000 nm. In practice of the invention, for example, cholesterol reflectance or transmittance data can be obtained at about 1720 or 2300 nm, and reference measurements taken at about 1620 or 1820 for the 1720 nm data, or at about 2200 or 2400 for the 2300 nm data, the reference data being obtained at wavelengths that are relatively insensitive to cholesterol content.

In another aspect of the invention, an analytic apparatus and method are described employing a multi-wavelength illumination source, a wavelength-specific detector array and a reflectance or transmittance ratio analyzer. The illumination source illuminates a material sample at a plurality of discrete wavelengths selected from the near infrared region, preferably in a narrowed window about 100-200 nm wide.

The detector array detects the light effected (i.e., reflected or transmitted) by the sample, converts the detected light into electrical signals indicative of the intensity of the effected light at each selected wavelength and transmits the converted signals to a reflectance or transmittance ratio analyzer. The analyzer then derives a ratio for at least two of the detected wavelengths, such that the ratio can be compared with predetermined values to non-invasively detect the concentration of blood-cholesterol in a subject's circulatory system.

By performing a ratio analysis in a narrowed window at longer wavelengths, the preferred embodiment eliminates background and patient-dependent (e.g., skin pigmentation, thickness and vascular) factors that might otherwise interfere with accurate measurements. Other wavelength combinations are also within the scope of the invention.

In one particular embodiment of the invention, the illumination source includes at least two laser diodes, producing light at distinct wavelengths, with a reference selected at approximately 1620 or 1820 nm and a cholesterol data wavelength selected at approximately 1720 nm. This embodiment is particularly well-suited to providing a system for detecting cholesterol in blood circulating through a surface vein, or in a fingernail bed, due to the penetration of near infrared wavelengths of light through human tissue, e.g., skin and the like.

In one method of the invention, a surface vein in a human subject is illuminated with infrared light (i.e., at about 1620 or 1820 nm), and a non-invasive reference reading is taken so as to establish a baseline background reflectance or transmittance value. The vein is also illuminated with light at a second (data) wavelength (i.e., at about 1720 nm) and a second non-invasive reading is taken, so as to establish a blood-cholesterol reflectance or transmittance level. The ratio of these readings (e.g. data/reference) is compared to known (e.g., stored in a look-up table) ratios relating to known cholesterol levels, and a cholesterol level for the non-invasive sampling is thereby determined.

The present invention is an improvement over the prior art in that it can, with improved accuracy, non-invasively, quickly and easily detect and/or quantify blood-cholesterol levels. In this way, the invention eliminates the problems of non-continuous data, subject discomfort and/or potential exposure to infectious diseases.

The invention will next be described in connection with certain preferred embodiments; however, it should be clear that various additions, subtractions and modifications can be made without departing from the spirit or scope of the invention. For example, although the invention is illustrated in connection with a blood analysis system, various alternative embodiments can also be devised.

For example, although the illustrated embodiment shows a system with a fiber optic bundle for delivery of six distinct wavelengths of light, it should be clear that the number of interrogation wavelengths, the size and shape of the sampling head, and the means for transmitting the light to and from the sample, can be varied to meet particular needs and applications. For example, in monitoring blood-cholesterol levels, as few as two wavelengths may be used. Moreover, a single fiber can be used for transmission and detection of multiple interrogation wavelengths. Additionally, although lasers are described as preferred light sources, other illumination means, including non-coherent, discrete wavelength light sources, can be employed.

DETAILED DESCRIPTION

Figure 1:
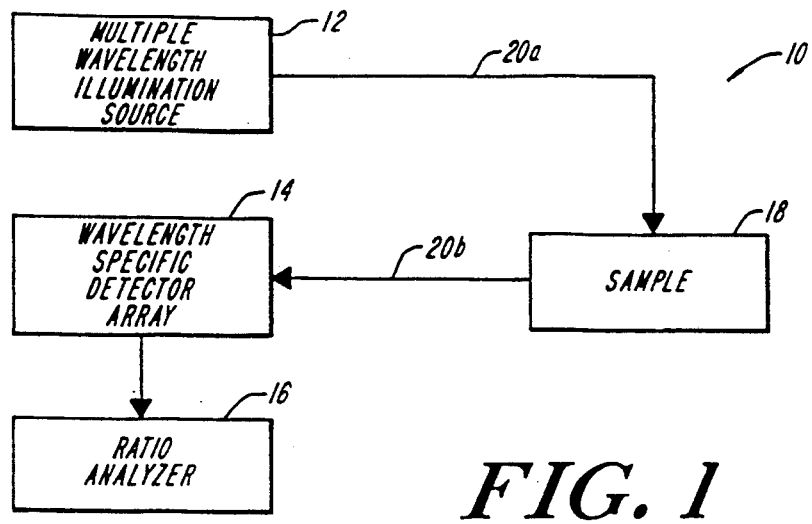
FIG. 1 is a schematic block diagram of an analytic apparatus according to the invention.

A schematic block diagram of an analytic apparatus 10 according to the invention is shown in FIG. 1. Apparatus 10 includes a multiple wavelength illumination source 12, a wavelength specific detector array 14, and a reflection ratio analyzer 16. Illumination source 12 can be a single, multi-wavelength laser diode or a series of discrete diode elements, each emitting a distinct wavelength of light selected from the near infrared region to illuminate a blood sample 18 via optical path 20a. Detector array 14 detects effected light, i.e., light reflected from sample 18 through optical path 20b. The detector array 14 converts the reflected light into electrical signals indicative of the intensity of the effected light at each wavelength and transmits the converted signals to the reflection ratio analyzer 16. Analyzer 16 processes the electrical signals and derives a reflectance ratio for at least two of the wavelengths. Analyzer 16 then compares the calculated reflectance ratio with predetermined values to detect the concentration and/or presence of cholesterol, and perhaps also other analytes, in the blood sample 18.

Figure 2:
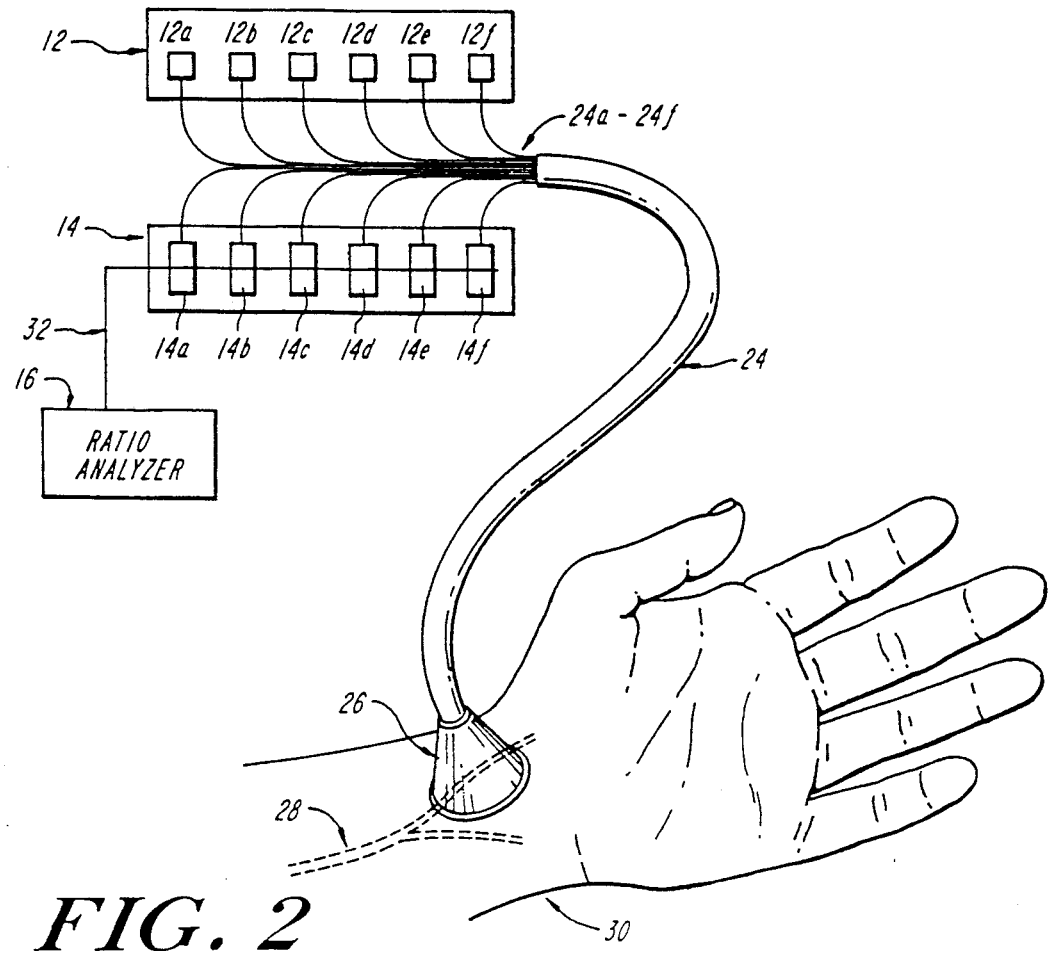
FIG. 2 is a schematic diagram of the apparatus according to the invention particularly adapted for non-invasive detection of cholesterol in a subject's blood.

An embodiment of analytic apparatus 10 particularly adapted to provide a system for detecting cholesterol in blood circulating through a surface vein is shown in FIG. 2. As can be seen from FIG. 2, laser diode elements 12a-12f comprise a multiple wavelength illumination source 12, which provides light at a series of skin penetrating wavelengths (between about 1600 and 1800 nm for cholesterol detection). Diode elements 12a-12f each transmit a predetermined wavelength of light via corresponding optical fiber elements 24a-24f and sampling head 26, to vein segment 28 of wrist 30. (Alternatively, light at various wavelengths can be emitted by one multiple-wavelength laser diode and transmitted via a single optical fiber.) The discrete wavelengths of laser light automatically pass through the tissue of wrist 30 and illuminate the blood circulating in surface vein 28.

For example, at least one of the diode elements 12a-12f can transmit interrogating radiation at a wavelength about 1720 nm and another of the diode elements 12a-12f can transmit radiation at 1600 or 1800 nm. In some instances, it may also be preferable to take at least one further reading using another of the diode elements 12a-12f to provide additional baseline data for analyte discrimination.

Following irradiation by the diode elements 12a-12f, a fraction of the transmitted light is reflected back from the blood circulating in surface vein 28 along optical fiber elements 24a-24f. (In one embodiment, each optical fiber element 24a-24f carries a reflected light signal having the same wavelength as the light originally transmitted along it.) Diode detectors 14a-14f receive the reflected light from the optical fiber elements 24a-24f and convert these light waves into a series of electrical signals indicative of the intensity of each of the reflected wavelengths of light received from surface vein 28. For example, if laser diode element 12a originally transmitted light of wavelength 1720 nm along optical fiber element 14a, then optical fiber element 14a will carry reflected light of wavelength 1720 nm back to diode detector element 22a.

As shown in FIG. 2, diode detector elements 14a-14f transmit the electrical signals indicative of the intensity of the reflected light to reflection ratio analyzer 16 along electrical connection 32. Analyzer 16 compares the electrical signals received from diode detector elements 14a-14f to derive a reflectance ratio for at least two of the transmitted wavelengths of light, such that the ratio can be compared to predetermined values to detect the presence of cholesterol in the blood flowing through vein 28. Analyzer 16 then can be employed to determine the presence and concentration of cholesterol alone or along with other blood analytes.

Figure 3:
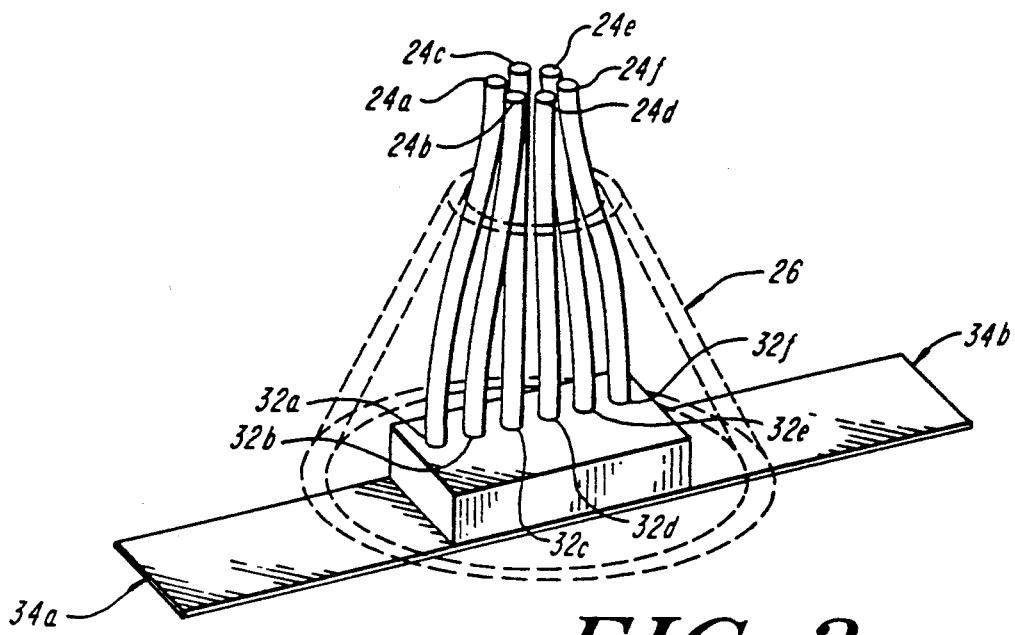
FIG. 3 is a detailed view of the sampling head assembly of the apparatus of FIG. 2.

FIG. 3 shows a more detailed view of the sampling head 26 of FIG. 2. As can be seen from FIG. 3, optical fiber elements 24a-24f of optical fiber bundle 24 are adapted to extend through a corresponding set of holes 32a-32f in the sampling head 26, thus, facilitating alignment of optical fiber elements 24a-24f along a surface vein or other vascular region. Sampling head 26 also comprises taping flanges 34a and 34b located at opposed ends of sampling head 26, providing a means for affixing sampling head 26 above the surface.

Figure 3A:
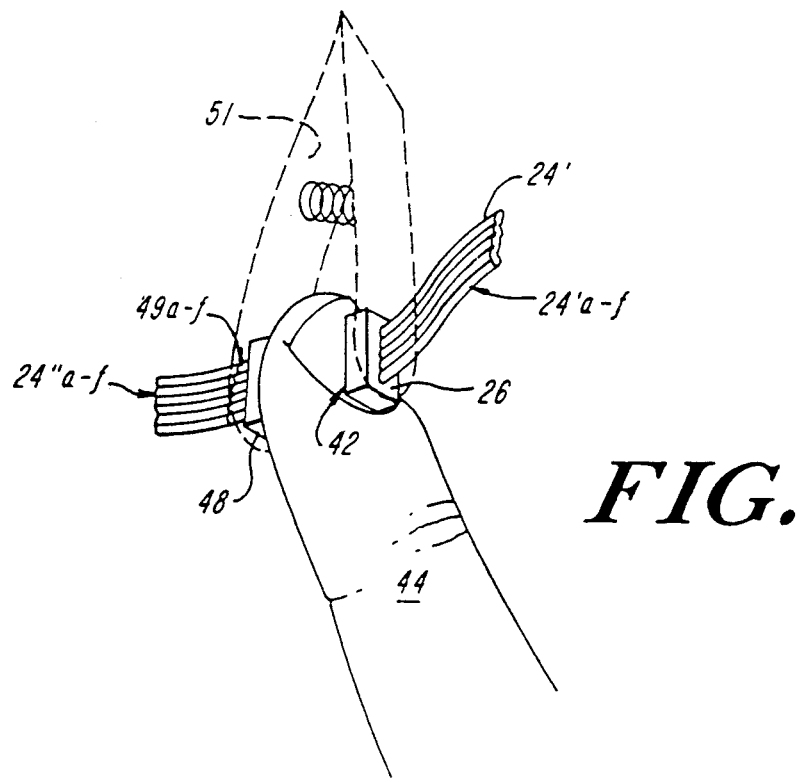
FIG. 3A is a view of an alternative embodiment of the sampling head assembly and detector.

FIG. 3A shows an alternative embodiment of a sampling head 26 of FIG. 2. Optical fiber elements 24'a-f of optical fiber bundle 24' coupled to source 12 are adapted to extend through a corresponding set of holes in the sampling head 26A, thus facilitating alignment of the optical fiber elements at the surface 42 of a finger 44 immediately above a nailbed 46. The light from fibers 24'a-f is transmitted through the finger and absorption is measured by applying a detector 48 on the opposite side of the finger. The detector 48 can employ a corresponding series of optical fibers 24"a-f and, optionally, a corresponding set of wavelength-specific filters 49 a-f, as shown, or, in a more simple embodiment, a broadband detector can be used and rely, for example, on sequential emissions of specific interrogation wavelengths by the illumination means.

The sampling head 26A and detector 48 can be attached to the fingertip by a clip 51, as shown, or by straps located at opposed ends of sampling head 26A, in a manner similar the attachment means of FIG. 3, to provide a means for affixing the apparatus about the finger. (In other transmittance measuring embodiments, the sampling head 26A and detector 48 can be disposed in other locations as well, such as an earlobe, toe or the like.)

Figure 4:
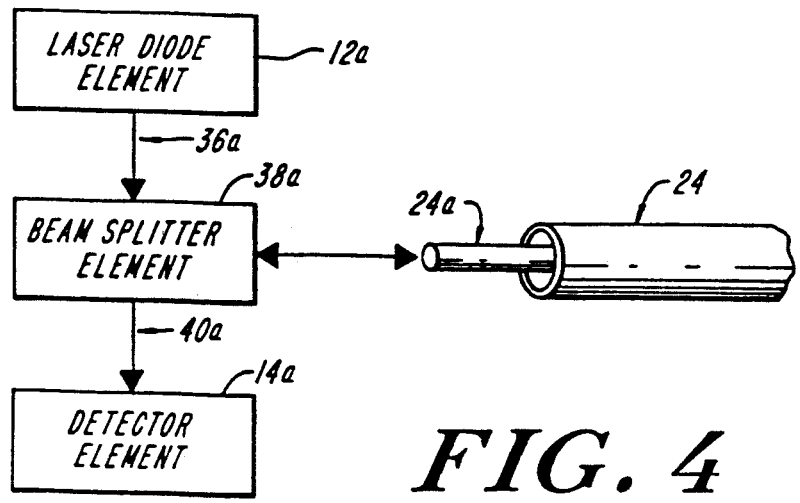
FIG. 4 is a more detailed illustration of an individual optical fiber and its connection to an illumination source and a detector element according to the invention.

FIG. 4 is a more detailed illustration of an individual optical fiber 24a and its connection to an illumination source 12a and a detector element 14a in a reflection-mode analysis system according to the invention. Since each of optical fiber elements 24a-24f is identically adapted, only optical fiber element 24a is shown. Laser diode element 12a is connected to optical fiber element 24a via optical fiber element 36a through optical splitter 38a. Diode detector element 14a is connected to optical fiber element 24a via optical fiber element 40a, also through optical splitter 38a. Optical splitter element 38a (and corresponding elements 38b-38f, not shown) enable dual usage of optical fiber elements 24a-24f so that the light emitted by laser diode elements 12a-12f and not absorbed by the tissue sample travels along the same optical fiber elements 24a-24f.

Figure 5:
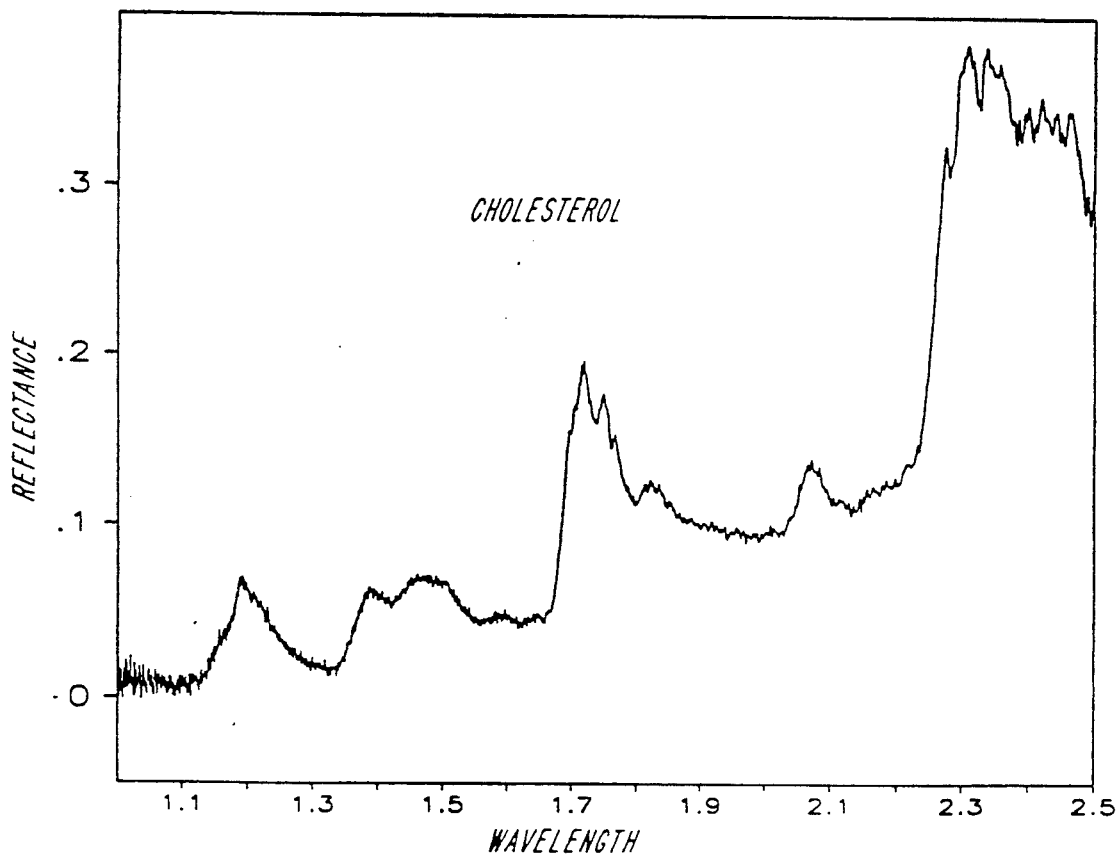
FIG. 5 is a graph of the reflectance of cholesterol over a spectrum of about 1000 to 2500 nm.

FIG. 5 is a graph of the reflectance of cholesterol, from 1000 to 2500 nm. As can be seen, cholesterol has a reflectance peaks at about 1720 and 2300 nm, which can be used as the wavelengths for collection of cholesterol reflectance or transmittance data. The signal trails off substantially on either side of the peak, so that signal level differences even in this narrow window provide useful data for the above rationing process.

Figure 6:
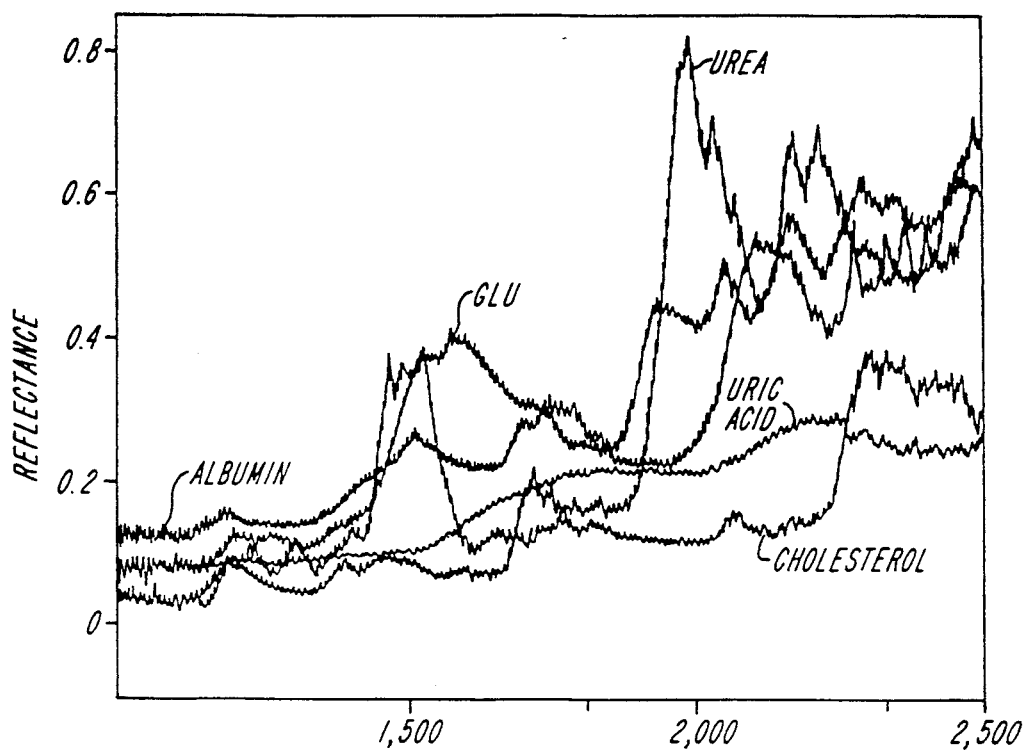
FIG. 6 is a graph of absorbance (in arbitrary units) exhibited by albumin, glucose, urea, uric acid and cholesterol in a blood sample illuminated over the range of 1000 to 2500 nm.

FIG. 6 is a graph of reflectance exhibited by albumin, glucose, urea, uric acid and cholesterol in a blood sample illuminated over the range of 1000 to 2500 nm. At about 1720 nm and 2300 nm, cholesterol reaches a reflectance peak, while the other analytes are in a more gradual mode. After determination of the level of other analytes of interest (albumin, uric acid, glucose, urea) a subtractive process can be used to obtain the detection signal for cholesterol.

The cholesterol data signal is obtained and is compared to the reference wavelength and a ratio is obtained by the ratioing described above, and then the ratio is compared to data stored in a lookup table to obtain a cholesterol reading for the subject. If a narrow detection window of about 100 nm is used, e.g., 1720 compared to 1620 or 1820, for example, this has the benefit of substantially reducing scattering effects. However other wavelengths can be selected to define a broader window but which still facilitates useful cholesterol readings in practice of the invention.

Thus, the present invention benefits from the recognition that there is a general class of scattering phenomena which can effect reflectance readings. These scattering phenomenena are principally due to size issues, i.e., big molecules making up the skin, the blood, and the cells themselves. Other artifacts in the detected reflectance signals can arise from skin pigmentation and gross variations in blood constitution from patient to patient.

Furthermore, given that scattering increases as wavelength shortens, we have selected a preferred narrow window, with the cholesterol absorbance wavelength at about 1720 nm or 2300 nm. The invention can therefore reduce scattering by selection of relatively long wavelengths and by selection of as narrow a window as possible. Nevertheless, where necessity dictates, such as where other analytes are present, other wavelengths in the near infrared range may also be used in useful practice of the invention.

In view of the above, these selected values exploit the foregoing properties of cholesterol by taking the ratio of light reflected from or transmitted by blood at a reference near infrared wavelength where cholesterol absorption is minimal, and at a data near infrared wavelength where reflectance or transmittance will be dependent on the concentration of cholesterol present in the irradiated region, with minimized effect of light scattering on the subsequent reflectance ratioing.

Light sources, such as laser diodes or light-emitting diodes, at the preferred wavelengths disclosed herein may be used, either custom designed or as tuned or filtered in a conventional manner.

As indicated above, the invention may be embodied in other specific forms without departing from the spirit or the essential characteristics thereof, and that both reflectance and transmittance apparatus and process are contemplated herein. The present embodiments are to be considered as illustrative and not restrictive. The scope of the invention is indicated by the appended claims, rather than by the foregoing description, and all changes which come within the meaning and range of equivalent of the claims are therefor intended to be embraced therein.

What is claimed is:

1. A blood-cholesterol detection apparatus comprising:
   illumination means for non-invasively illuminating an in vivo blood sample in a patient at a plurality of infrared wavelengths for generating a background reference signal and a cholesterol data signal;
   detector means for non-invasively detecting light effected by said sample at least one data wavelength and at one reference wavelength for each data wavelength of said plurality of wavelengths and for converting said detected light into electrical signals, said electrical signals being indicative of the intensity of said effected light at said data and reference wavelengths, said data and reference wavelengths being separated by no more than about 100 nm; and
   analyzing means for receiving and comparing said electrical signals to derive a ratio for at least said data and reference wavelengths, such that said ratio can be compared with predetermined values associated with known blood-cholesterol concentrations so as to detect the cholesterol level in said sample.

2. The apparatus of claim 1 wherein said illumination means further comprises at least two light sources, each producing light at a distinct wavelength within a window at about 1620–1820 nm.

3. The apparatus of claim 2 wherein a first one of said sources is operable at about 1720 nm.

4. The apparatus of claim 1 wherein said illumination means further comprises at least two light sources, each producing light at a distinct wavelength within a window at about 2200–2400 nm.

5. The apparatus of claim 4 wherein a first one of said sources is operable at about 2300 nm.

6. The apparatus of claim 1 wherein said illumination means further comprises at least two light sources, each of said light sources producing light at a distinct data wavelength, one of which being at about 1720 nm and the other at about 2300 nm, for making separate measurements of cholesterol absorption data.

7. The apparatus of claim 1 wherein said illumination means further comprises at least two light sources, each producing light at a distinct wavelength with a first one of said sources operable at about 100 nm away from a second one of said sources.

8. The apparatus of claim 1 wherein said analyzing means further comprises means for quantifying the concentration of cholesterol in said sample.

9. The apparatus of claim 1 wherein said detector means detects light reflected by said sample at said plurality of wavelengths.

10. The apparatus of claim 1 wherein said detector means detects light transmitted by said sample at said plurality of wavelengths.

11. A method for detecting blood-cholesterol levels in vivo, comprising the steps of:
    illuminating a source of blood non-invasively through the tissue of a subject with light at a plurality of infrared wavelengths for generating a background reference signal and a cholesterol data signal;
    detecting said infrared light at at least one data wavelength and at one reference wavelength for each data wavelength of said plurality of wavelengths as effected by said blood and converting said detected light into electrical signals indicative of the intensity of said effected light at said wavelengths, said data and reference wavelengths being separated by no more than about 100 nanometers;
    analyzing said electrical signals to derive a ratio for said data and reference wavelengths; and
    comparing said ratio to a predetermined value to detect the presence of cholesterol in said blood.

12. The method of claim 11 wherein the step of comparing includes detecting the concentration of cholesterol in said blood.

13. The method of claim 12 wherein said step of illuminating further comprises illuminating said blood source with at least two light sources, each producing light at a distinct cholesterol data wavelength, one of said at least two light sources being at about 1720 nm and the other at about 2300 nm.

14. The method of claim 11 wherein said step of illuminating further comprises the step of illuminating the blood source at a wavelength at about 1720 nm.

15. The method of claim 11 wherein said step of illuminating further comprises the step of illuminating the blood at a wavelength at about 2300 nm.

16. The method of claim 11 wherein said step of analyzing further comprises the step of quantifying the concentration of cholesterol in said sample.

17. The method of claim 11 wherein said step of detecting further comprises the step of detecting light reflected by said sample at said plurality of wavelengths.

18. The method of claim 11 wherein said step of detecting further comprises the step of detecting light transmitted by said sample at said plurality of wavelengths.

19. A blood-cholesterol detection apparatus comprising:
    illumination means for non-invasively illuminating an in vivo blood sample in a patient at a plurality of infrared wavelengths, said illumination means further comprising at least two light sources, with a first one of said sources being operable at a first one of said wavelengths and a second one of said sources being operable at a second one of said wavelengths about 100 nm away from said first wavelength, for generating a background reference signal and a cholesterol data signal within a narrow measurement window;
    detector means for non-invasively detecting light effected by said sample at said reference and data wavelengths and for converting said detected light into electrical reference and data signals, said electrical signals being indicative of the intensity of said effected light at said first and second wavelengths; and
    analyzing means for receiving and comparing said electrical signals to derive a ratio for said first and second wavelengths, such that said ratio can be compared with predetermined values associated with known blood-cholesterol concentrations so as to detect the cholesterol level in said blood sample.

20. The apparatus of claim 19 wherein said sources each produce light at a distinct wavelength within said window at about 1620–1820 nm.

21. The apparatus of claim 20 wherein one of said sources is operable at about 1720 nm.

22. The apparatus of claim 19 wherein said sources each produce light at a distinct wavelength within said window at about 2200-2400 nm.

23. The apparatus of claim 22 wherein one of said sources is operable at about 2300 nm.

24. The apparatus of claim 19 wherein one of said light sources operates at about 1720 nm, further comprising at least two additional light sources one of which operating at about 2300 nm, for making separate measurements of cholesterol absorption data at 1720 and 2300 nm.

25. A method for detecting blood-cholesterol levels in vivo, comprising the steps of:

illuminating a source of blood non-invasively through the tissue of a subject with at least two light sources, each producing light at a distinct infrared wavelength within a window at about 100 nm wide, for generating a background reference signal and a cholesterol data signal;

detecting said infrared light as effected by said blood and converting said detected light into electrical signals indicative of the intensity of said effected light at said wavelengths;

analyzing said electrical signals to derive a ratio for said wavelengths; and comparing said ratio to a predetermined value to detect the presence and concentration of cholesterol in said blood.

26. The method of claim 25 wherein said step of illuminating further comprises the step of illuminating the blood at a wavelength at about 1720 nm.

27. The method of claim 25 wherein said step of illuminating further comprises the step of illuminating the blood at a wavelength at about 2300 nm.

* * * * *